United States Patent [19]
Imbert et al.

[11] Patent Number: 6,107,284
[45] Date of Patent: *Aug. 22, 2000

[54] WATER-SOLUBLE DERIVATIVES OF EPIPODOPHYLLOTOXIN, PROCESS FOR THEIR PREPARATION, THEIR USE AS MEDICINAL PRODUCTS AND THEIR INTENDED USE IN ANTI-CANCER TREATMENTS

[75] Inventors: Thierry Imbert, Viviers-les-Montagnes; Yves Guminski, Lagarrigue; Barbara Monse; Bridget Hill, both of Castres; Jean-Pierre Robin, Le Mans, all of France

[73] Assignee: Pierre Fabre Medicament, Boulogne, France

[*] Notice: This patent issued on a continued prosecution application filed under 37 CFR 1.53(d), and is subject to the twenty year patent term provisions of 35 U.S.C. 154(a)(2).

[21] Appl. No.: 08/817,907

[22] PCT Filed: Oct. 20, 1995

[86] PCT No.: PCT/FR95/01388

§ 371 Date: Apr. 21, 1997

§ 102(e) Date: Apr. 21, 1997

[87] PCT Pub. No.: WO96/12727

PCT Pub. Date: May 2, 1996

[30] Foreign Application Priority Data

Oct. 21, 1994 [FR] France .................................. 94 12597

[51] Int. Cl.$^7$ ............................ A61K 31/70; C07H 15/24
[52] U.S. Cl. ............................ 514/27; 514/33; 536/17.1; 536/17.2; 536/17.5; 536/17.6; 536/18.1
[58] Field of Search .................................. 514/25, 27, 33; 536/17.6, 17.1, 18.7, 17.2, 17.5, 18.1

[56] References Cited

U.S. PATENT DOCUMENTS 5,041,424  8/1991  Saulnier et al. .......................... 514/27

FOREIGN PATENT DOCUMENTS

| 0 415 453 | 3/1991 | European Pat. Off. . |
| 0 445 021 | 9/1991 | European Pat. Off. . |
| 2 207 674 | 2/1989 | United Kingdom . |
| WOA94 14829 | 7/1994 | WIPO . |

*Primary Examiner*—Elli Peselev
*Attorney, Agent, or Firm*—Rockey, Milnamow & Katz, Ltd.

[57] ABSTRACT

Water-soluble derivatives of epipodophyllotoxin, process for their preparation and their use for the treatment of rheumatoid arthritis, complaints caused by human papilloma virus and cancer.

14 Claims, No Drawings

WATER-SOLUBLE DERIVATIVES OF EPIPODOPHYLLOTOXIN, PROCESS FOR THEIR PREPARATION, THEIR USE AS MEDICINAL PRODUCTS AND THEIR INTENDED USE IN ANTI-CANCER TREATMENTS

Among the class of epipodophylloids, certain compounds such as etoposide or teniposide, which are semisynthetic compounds derived from epipodophyllotoxin, obtained from natural lignan, are used in the preparation of medicinal products for treating many forms of cancer. They are currently considered as major products of the therapeutic arsenal.

Among the various cancers treated with compounds of this type, mention may be made of alveolar lung cancer, embryonic tumors, neuroblastomas, cancer of the kidney, lymphomas, Hodgkin's disease, acute leukemias, and even breast cancer. Etoposide is advantageously used in combination with other anticancer products and in particular platinum derivatives such as cisplatin.

The major drawback of this derivative, and likewise of its related derivative teniposide, is its lack of water-solubility. No water-soluble forms for intravenous administration exist on the market. On the contrary, the dissolution is currently carried out in partially non-aqueous solvents, requires administration by slow infusion and gives rise to certain undesirable or even toxic effects. There is thus a need for water-soluble forms for products derived from this class of compounds in order to improve the administration to the patient, as well as its bioavailability. The present invention thus relates to etoposide derivatives which are water-soluble by means of the presence of phosphate or carboxylate functional groups whose organic or inorganic addition salts form soluble species in water. This aqueous formulation has the advantage of being less toxic and easier to administer than the forms currently marketed.

The preparation of etoposide derivatives has given rise to considerable research and many patient, and in particular 2" and 3" diester and 2", 3" and 4' triester derivatives of etoposide have been claimed in patent FR 2,699,535-A1. Some of these derivatives have shown activity equal to or greater than etoposide and less toxicity. An additional improvement is now provided by means of a solubility in water which imparts to them ease of administration and leads to the expectation of increased bioavailability by better passage across the various biological membranes.

The literature mentions patents relating to compounds similar to etoposide in which it is sought to improve the water-solubility, in particular (U.S. Pat. No. 4,904,768, EP 0,369,369-A2, EP 0,196,618-A1, EP 0,320,988, EP 0,415,453-A2).

The advantage of modifying the water-solubility of the compounds by means of phosphate groups has been used favorably in a few cases both in the field of anticancer agents WO 8707609 and in the field of analgesics (BE 893,563) but, despite everything, there is nothing to suggest that the compound thus obtained can fully retain an advantageous biological activity of its own as well as the activity of the derivative from which it is obtained.

It has been found that phosphate and carboxylate derivatives possess a water-solubility which allows administration via an injectable route, and moreover exhibit improved anticancer activity relative to etoposide. The present invention therefore relates to a compound of general formula I

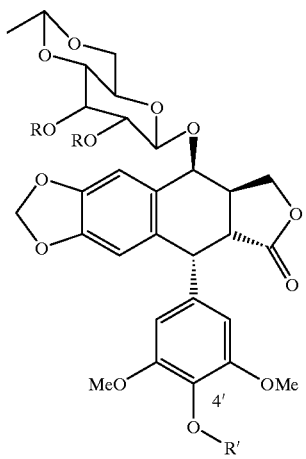

in which R' represents either a hydrogen atom or a phosphate monester group or a carbamate group of —CO—N—$(R_1R_2)$ type where $N(R_1R_2)$ represents aminodiacetic groups and a polycyclic amine such as 3-aminoquinuclidine or an acyl group of phosphonoacetic type $H_2O_3P$—$CH_2$—CO or a radical R, R represents an acyl group of formula A—Z—$CH_2$—CO where Z represents an oxygen or sulfur atom, an $SO_2$ group or a linear or branched $C_{1-4}$ alkylene, in this case A represents a substituted or unsubstituted phenyl ring, on condition that:

in the case where R'=R, that is to say triacyl derivatives, A represents an aromatic ring possessing a salifiable function, with the exception of 4-hydroxyphenyl, in the case where R' R, A represents a benzyl, naphthyl, heteroaryl or phenyl residue which is substituted or unsubstituted, it being possible in this case for the phenyl to be substituted one, two, three, four or five times, irrespective of their position on the aromatic ring, with identical or different groups chosen from groups such as halogens, F, Cl, Br, linear or cyclic $C_{1-6}$ alkoxy, $C_{1-6}$ alkyl, methylenedioxy, $OCF_3$, $CF_3$, $NO_2$, CN, $OCH_2Aryl$, OH, $OPO_3H_2$, $CH_2PO_3H_2$, $PO_3H_2$, $OCH_2CO_2H$, COOH, $CH_2COOH$, $COCH_3$, CHO, A-Z may also represent an $OCH_2CO_2H$, $SO_2CH_2COOH$ or $PO_3H_2$ group, as well as its salts with therapeutically acceptable and water-soluble, inorganic or organic acids or bases, with the exception of the compounds for which R=H, and Z represents an oxygen atom or a sulfur atom, and A represents an aryl chosen from phenyl, phenyl-alkyl, which is $C_1$–$C_4$ linear or branched, and naphthyl radicals, and these same radicals substituted with one to three substituents chosen from linear or branched $C_1$–$C_4$ alkoxy radicals optionally perhalogenated with chlorine or fluorine atoms, linear or branched $C_1$–$C_4$ alkyl radicals and halogen atoms, in particular chlorine or fluorine.

The compounds of general formula I will advantageously be chosen with R' representing a phosphate monester ($PO_3H_2$) or carbamate $CONHR_1R_2$ group and $NR_1R_2$ representing an aminodiacetic or 3-amino-quinuclidine group, R' also representing a phosphonoacetic group and their salts.

R is preferably chosen from the radicals: phenoxyacetyl, 3,4-methylenedioxyphenoxyacetyl, 4-methoxyphenoxyacetyl, 4-hydroxyphenoxyacetyl, 4-phosphoneoxyphenoxyacetyl, 4-carboxymethylphenoxyacetyl, 4-carboxymethoxyphenoxyacetyl, 4-carboxyphenoxyacetyl, 4-trifluoromethylphenoxyacetyl, 4-trifluoromethoxyphenoxyacetyl, 4-chlorophenoxyacetyl, 4-nitrophenoxyacetyl, 4-fluorophenoxyacetyl, cyclohexloxyacetyl, phenylsulfonylacetyl, pentafluorophenoxyacetyl, 2- and 4-formylphenoxyacetyl, 4-cyanophenoxyacetyl.

The present invention also relates to processes for the preparation of a compound of formula I, represented in Scheme 1 (route A), for which a glycosylated intermediate of general formula II

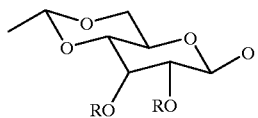

II is reacted with an intermediate of general formula III to give an intermediate IV

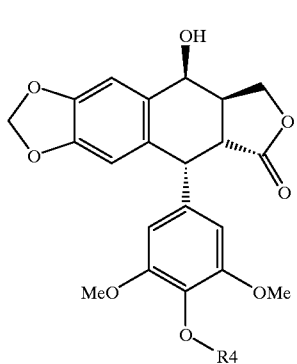

III

R have the above meanings. $R_4$ is a protecting group, for example benzyloxycarbonyl or a carbamate residue. This preparation process is described in the prior patent FR 2,699,535 in Example 17. In order to give a compound of formula IV in which $R_4$ is a protecting group and R defined above. This derivative IV is deprotected in its position 4' ($R_4$), either by hydrogenolysis or by weakly basic hydrolysis to give the derivative I (R'=H). It is also possible to prepare the compounds of formula I where R'=R by this method, using the intermediate of formula III in which $R_4$ represents an acyl group R, this method is also described in the prior patent FR 2,699,535 in Example 1. Depending on the compatibilities of the substituents R of the glucosyl, it is also possible to synthesize the compounds of formula I from etoposide itself (Route B).

In a first step, etoposide may be protected in position 4' ($R_4$) with a group $R_4$=benzyloxycarbonyl, or with a quinuclidine carbamate group ($R_4$=CONH$_3$-quinuclidinyl) obtained by successive reaction of phosgene followed by 3-aminoquinuclidine on etoposide, to give the intermediate V.

In general, the intermediates V are acylated with acid chlorides derived from the groups R defined above (formed by the action of oxalyl chloride), in the presence of pyridine, in methylene chloride at low temperature, with the proviso that the other functions of the group R are inert under these conditions, otherwise, the phenolic, carboxylic or phosphonic substituents are protected in the form of benzyl esters or ethers respectively, thereby allowing unblocking, at the next stage in the synthesis, by hydrogenolysis (V giving I R'=H). The derivatives for which R'=R are prepared from etoposide by triacylation on the positions 2", 3" and 4' (route C).

In the case of the functional derivatives R which are sensitive to the hydrogenolysis conditions such as, for example, but not exclusively, the presence of Cl or NO$_2$, the protecting group chosen on the position 4' may be a carbamate derivative of CONH—3-quinuclidinyl type or a carbonate or an ester of low molecular weight, such as chloroacetates, which may be cleaved subsequently, inter alia, under weakly basic conditions, for instance an aqueous sodium bicarbonate solution at low temperature, without influencing the stereochemistry of the trans lactone.

The final step I (R'=H) giving I (R'= H) consists of a phosphorylation to form a phosphate monoester of the phenol or phenols with POCl$_3$ in the presence of pyridine, followed by a slow hydrolysis in aqueous acidic medium.

Derivatives possessing a diacetic carbamate residue of R'=CON(CH$_2$CO$_2$H)$_2$ type in position 4' are prepared by the action of phosgene on the compound of formula I (R'=H) to form the non-isolated chlorocarbonate intermediate (R'= COCl), after which it is reacted with the benzyl diester of aminodiacetic acid, followed by a hydrogenolysis in order then to release the acidic functions in free form.

The phosphonoacetic derivatives in position 4' are obtained by reacting the free phenol in this position with diethylphosphonoacetyl chloride (Synthesis 1978, 131) or dibenzylphosphonoacetic acid (Tet. Let. 1974, No. 9, 711), after which the phosphonic ester functions are hydrolysed with trimethylsilyl bromide, in the presence of pyridine in acetonitrile, in the case of the ethyl esters, or by hydrogenolysis, in the case of the benzyl esters. The derivatives of formula I where R'=R, that is to say those possessing the same acyl substitution on the positions 2", 3" and 4', are obtained, via route C, by triacylation of etoposide itself with acyl groups AZCH$_2$CO have a carboxylic function on the group A defined above, protected for example in benzyl ester form, which is subsequently deprotected by hydrogenolysis.

The carboxylic derivatives, or the phosphate or phosphonate derivatives, thus obtained are salified in water optionally in the presence of an organic cosolvent, by addition of organic or inorganic bases in stoichiometric proportion relative to the acidities present, and, for example, with N-methylglucamine, triethanolamine, lysine, etc.

The amorphous or crystalline salts are obtained by simple freeze-drying.

Scheme 1

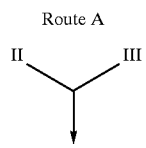
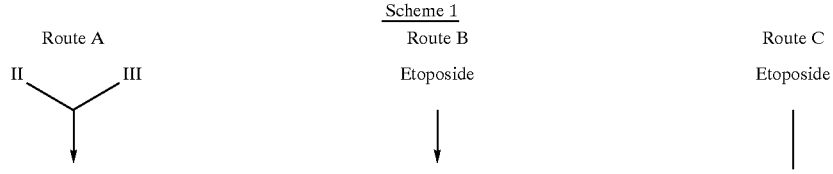

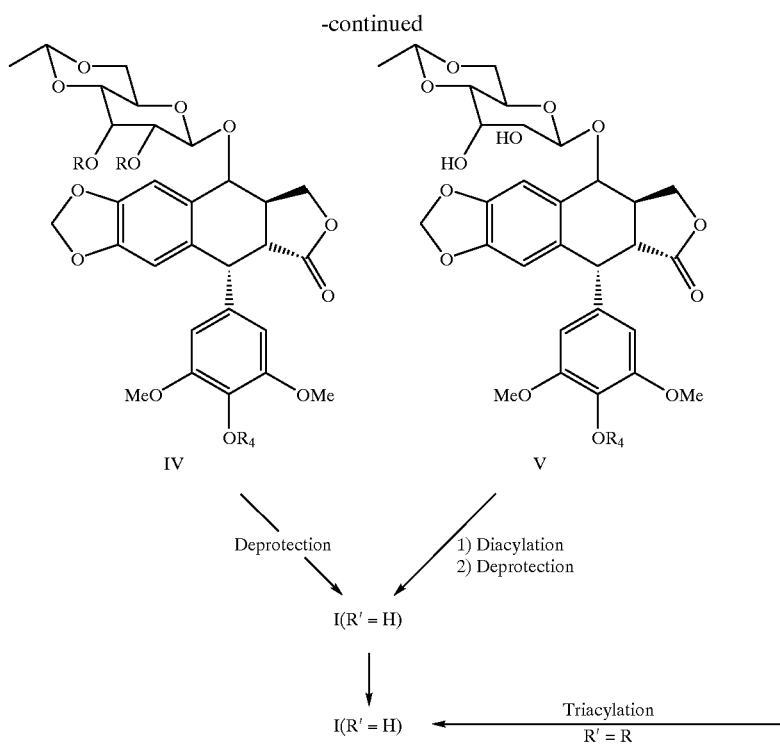

Measurement of the Water-Solubility

The solubility in water of the salts of the phosphate or carboxylate derivatives by addition of physiologically acceptable organic amines such as, for example, N-methylglucamine, triethanolamine or lysine, or the salts with inorganic cations such as sodium, obtained in lyophilized form or by extemporaneous addition of a base to the free acid compound, gave the following results by way of example.

TABLE II

| Compounds | Salt | % solubility (weight/volume) expressed in g per 100 ml of water |
|---|---|---|
| Example 1 | N-methylglucamine | 0.5 |
| Example 3 | N-methylglucamine | 5 |
| Example 4 | N-methylglucamine | 10 |
| Example 6 | N-methylglucamine | 10 |
| Example 6 | triethanolamine | 20 |
| Example 6 | lysine | 20 |
| Example 6 | Sodium | 1 |
| Example 7 | N-methylglucamine | 10 |
| Example 11 | N-methylglucamine | 10 |
| Example 21 | N-methylglucamine | 10 |
| Example 26 | N-methylglucamine | 10 |
| Example 27 | N-methylglucamine | 0.5 |

The derivatives thus prepared are stable under the usual temperature and neutral and acidic pH conditions. The phosphate derivatives on position 4' have a chemical stability such as to be able to lend themselves to different pharmaceutical formulations.

Biological Experimentation

The molecules were tested in vitro in biological experimentation and showed their value as anticancer agents in the following tests.

Measurement of the inhibition of the activity of topoisomerase II is made according to the procedure described in the literature: "Nuclear topoisomerase II levels correlate with the sensitivity of mammalian cells to intercalating Agents and Epipodophyllotoxins", I. D. Hickson et al., J. Biol. Chem. (1988), 263, 17724.

This measurement gave the following results.

TABLE I

| Compounds | Test of inhibition of the activity of topoisomerase II ($ED_{50}$ M) |
|---|---|
| Etoposide | $5.6 \times 10^{-5}$ |
| Etopofos | $>10^{-4}$ |
| Example 1 | $5.6 \times 10^{-6}$ |
| Example 3 | $3.2 \times 10^{-7}$ |
| Example 4 | $1.8 \times 10^{-6}$ |
| Example 6 | $3.2 \times 10^{-7}$ |
| Example 7 | $5.6 \times 10^{-5}$ |
| Example 11 | $5.6 \times 10^{-6}$ |
| Example 21 | $5.6 \times 10^{-6}$ |
| Example 26 | $5.6 \times 10^{-6}$ |
| Example 27 | $7.6 \times 10^{-7}$ |

Comparison of etoposide with its soluble 4'-phosphate analog: etopofos (U.S. Pat. No. 4,904,768) shows a loss of in vitro activity. Here, the compounds of the invention are found to be as active as, if not more active than, etoposide. The groups R and R' defined above impart to the compounds of the invention an increase by a factor of 10 to 100 in the inhibition of the enzymatic activity in vitro relative to etoposide.

In view of these results, the value of compounds having anticancer activity equal to or higher than that of etoposide, and less toxicity, on various forms of cancers, such as, in particular, alveolar lung cancer, embryonic tumors, neuroblastomas, cancer of the kidney, pediatric tumors, hodgkinian and non-hodgkinian lymphomas, acute leukemias, placental choriocarcinomas and mammary adenocarcinomas may be appreciated.

These derivatives may also be used in pathologies induced by human papilloma virus as well as rheumatoid arthritis which may or may not be associated with cancer pathologies.

Furthermore, these derivatives may be used to increase the therapeutic efficacy of topoisomerase II-inhibitor compounds and in particular the treatment of tumors which normally do not respond to the usual therapy, that is to say colorectal cancers and melanomas. Furthermore, the value of these products having, on the one hand, considerable water-solubility which allows ready intravenous and oral administration and, on the other hand, better bioavailability than that of etoposide, may be appreciated.

The present invention also relates to the pharmaceutical compositions comprising at least one compound of general formula I according to the invention and a suitable excipient.

The pharmaceutical compositions may be presented in a form which is suitable for administration via an injectable route or via the oral route in the form of capsules, gelatin capsules or tablets at a dosage of from 2 to 200 mg/m$^2$ via the injectable route and from 5 to 400 mg/m$^2$ per 24 h via the oral route.

By way of example and in a non-limiting manner, the following examples describe the preparation of the compounds of the invention:

EXAMPLE 1

Formula I

4'-demethyl-4-O-(2,3-bisphenoxyacetyl-4,6-ethylidene-β-D-glucosyl)epipodophyllotoxin-4'-deoxy-4'-phosphate.

To a solution of 4'-demethyl-4-O-(2,3-bisphenoxyacetyl-4,6-ethylidene-β-D-glucosyl)epipodophyllotoxin (1 g, 1.16 mmol) in 50 ml of THF at 10° C. are added 0.22 ml (2.33 mmol) of POCl$_3$ and then 0.5 ml (3.5 mmol) of triethylamine. Stirring is continued for 30 min at this temperature. Hydrolysis is then carried out by addition to the medium of 20 ml of N hydrochloric acid, followed by stirring overnight at room temperature. The reaction medium is extracted with ethyl acetate to obtain the phosphate derivative which crystallizes from isopropyl ether in quantitative yield.

The characteristics are as follows: m.p. °C. ~175° C. Anal. $C_{45}H_{45}O_{20}P.1.5H_2O$; MW=963.831

Calc. % C 56.07 H 5.02

Found % C 56.18 H 4.73

Mass spectrum (FAB) m/e 959 (M$^+$+Na)

1H 200 MHz NMR CDCl$_3$ δ 1.30 (3H, d, J=4.4 Hz, H$_S$"); 2.9 (1H, m, H$_3$); 3.1 (1H, m, H$_2$); 5.0 (1H, dd, J=8.8 Hz, H$_2$"); 5.3 (1H, dd, J~9.2 Hz, H$_3$"); 5.5 (1H, s, OCH$_A$O); 5.7 (1H, s, OCH$_B$O); 6.25 (2H, s, H$_2$,H$_6$); 6.44 (1H, s, H$_8$).

IR σ (KBr) 2941, 1774, 1599, 1487.

N-Methylglucamine Salt

The above phosphate derivative is suspended in water and 2 equivalents of N-methylglucamine in 0.1M solution in water are added. The solution is agitated by ultrasound and diluted to 200 ml. After filtration, the solution is chilled and then lyophilized for 12 h. The residue is then taken up in acetone and crystallized, filtered dried to give 350 mg of a white solid. m.p.≈135° C.

Anal. $C_{59}H_{79}N_2O_{30}P.H_2O$; MW=1345.256

Calc. % C52.68 H6.06 N2.08

Found % C52.69 H5.86 N1.68

IR σ (KBr) 3426, 1772, 1599, 1487.

NMR $^1$H 200 MHz CDCl$_3$ δ 1.22 (3H, d, J=4.8 Hz, H$_8$"); 2.3 (6H, s, NCH$_3$); 2.6–3.0 (2H, m, H$_2$–H$_3$); 5.36 (1H, dd, J=7.8 Hz, H$_3$"); 5.74 (1H, s, OCH$_A$O); 5.97 (1H, s, OCH$_B$O); 6.15 (2H, s, H$_2$,–H$_6$,); 6.5 (1H, s, H$_8$); 7.10 (1H, s, H$_5$); 6.65 (2H, d, J=8 Hz, Ortho Ar); 6.8 to 6.96 (2H, d, J=8 Hz ortho Ar and 2H, t, J=7 Hz, para Ar); 7.24 (4H, m, meta Ar).

Sodium Salt

The above phosphate derivative is stirred in solution in acetone with an ion exchange resin (Dowex 50×8–100) prepared by elution with N sodium hydroxide. The medium is diluted with water, filtered and concentrated. The aqueous residue is lyophilized to give the disodium salt.

m.p.°~190° C. Anal. $C_{45}H_{43}Na_2O_{20}P_3.3H_2O$; MW=1040.208

Calc. C51.96 H4.81

Found C51.56 H4.51

By the same method as that of Example 1, but using the corresponding intermediate compounds of formula I (R'=H), the following novel derivatives were prepared:

EXAMPLE 2

Formula I

4'-demethyl-4-O-(2,3-bis-cyclohexyloxyacetyl-4,6-ethylidene-β-D-glucosyl)epipodophyllotoxin-4'-deoxy-4'-phosphate Yield=90% m.p.°~160° C. Anal. $C_{45}H_{45}O_{20}P.H_2O$; MW=966.920

Calc. C55.89 H6.15

Found C55.70 H6.11

N-Methylglucamine Salt

4'-demethyl-4-O-(2,3-bis-cyclohexyloxyacetyl-4,6-ethylidene-β-D-glucosyl)epipodophyllotoxin4'-deoxy-4'-phosphate, bis(N-methylglucamine) salt.

Yield=50% m.p.° ~112° C. Anal. $C_{59}H_9.N_2O_{30}P.4H_2O$; MW=1411.420

Calc. C50.21 H7.07 N1.99

Found C50.16 H6.60 N2.30

EXAMPLE 3

Formula I

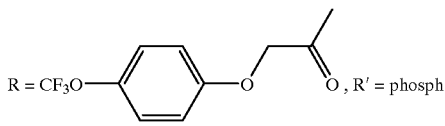

4'-demethyl-4-O-(2,3-bis-(4-trifluoromethoxyphenoxyacetyl)-4,6-ethylidene-β-D-gluocosyl)epipodophyllotoxin-4'-deoxy-4'-phosphate, bis(N-methylglucamine) Salt Yield=68% m.p. ~132° C. Anal. $C_{61}N_{77}N_2O_{32}F_6P.2.6H_2O$; MW=1541.840

Calc. C47.52 H5.37 N1.82

Found C47.15 H5.51 N2.11

EXAMPLE 4

Formula I

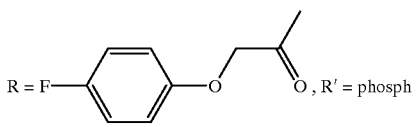

4'-demethyl-4-O-(2,3-bis(4-fluorophenoxyacetyl)-4,6-ethylidene-β-D-glucosyl)epipodophyllotoxin-4'-deoxy-4'-phosphate bis(N-methylglucamine) Salt Yield=60% m.p. ~130° C. Anal. $C_{59}H_{77}N_2O_{30}F_2P.2.7H_2O$; MW=1363.240

Calc. C50.17 H5.88 N1.98

Found C49.74 H5.67 N1.92

EXAMPLE 5

Formula I

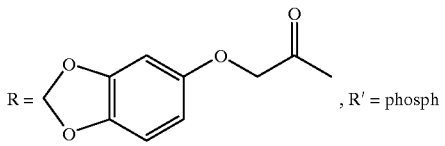

4'-demethyl-4-O-(2,3-bis(3,4-methylenedioxyphenoxyacetyl)-4,6-ethylidene-β-D-glucoxy)epipodophyllotoxin-4'-deoxy-4'-phosphate bis(N-methylglucamine) Salt Yield=50% m.p.~120° C. Anal. $C_{61}H_{79}N_2O_{34}P.H_2O$; MW=1433.274

Calc. C51.08 H5.70 N1.95

Found C50.68 H5.58 N1.94

EXAMPLE 6

Formula I

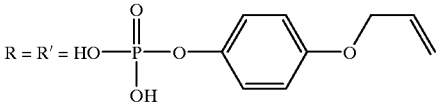

4'-(4-phosphonooxyphenoxyacetyl)-4'-demethyl-4-O-(2,3-bis(4-phosphonooxyphenoxyacetyl)-4,6-ethylidene-β-D-glucosyl)epipodophyllotoxin The phenolic derivative of formula I corresponding to R=R'=4-hydroxyphenoxyacetyl is described in patent FR 2,699,535-$A_1$ in Example 16, prepared via route A. 1 g of this derivative (9.6 mmol) is placed in 50 ml of THF at −10° C. under a nitrogen atmosphere and 1.2 ml (8.7 mmol) of triethylamine are added, followed by dropwise addition of 0.53 ml (5.8 mmol) of $POCl_3$, and stirring is continued for 30 min. After filtration of the triethylamine hydrochloride formed, the THF is evaporated off. The residue is taken up in 1N HCl and stirred at room temperature for 30 min. The white precipitate is filtered off, washed with water and dried under vacuum at 60° C. overnight. 800 mg of derivative are obtained in the form of free phosphate.

Yield=80%.

m.p. ~160° C. Anal. $C_{53}H_{53}O_{31}P_3$ MW=1278.898

Mass spectrum (FAB) m/e: 1277 ($M^+-1$)

IR (KBr) σ (cm-1) 3404, 1768, 1603, 1500, 1485, 1203, 1086.

NMR 1H 200 Mz (DMSO) δ: 1.23 (3H, d, J=4.26 Hz, $H_{8''}$); 3.03 (2H, m, $H_2$–$H_3$); 5.37 (2H, m, $H_{2''}$–$H_{3''}$); 5.77 (1H, s, O-$CH_{A-O}$); 5.97 (1H, s, O-$CH_{B-O}$); 6.3 (2H, s, $H_2$-$H_{6'}$).

The glucamine salt is prepared in a similar manner to that of Example 1, but with addition of 3 equivalents of N-methylglucamine. The compound is obtained directly after lyophilization, in a yield of 88%, giving the following analyses:

m.p. ~155° C. Anal. $C_{74}H_{104}N_3O_{46}P_3$ MW=1864.54

Calc. C47.67 H5.62 N2.25

Found C47.26 H5.62 N2.38

IR (KRr) σ (cm-1): 3458, 1768, 1604, 1500, 1485, 1199, 1084.

EXAMPLE 7

Formula I

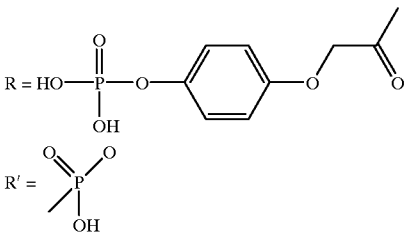

4'-demethyl-4-O-(2,3-bis(4-phosphonooxyphenoxyacetyl)-4,6-ethylidene-β-D-glucosyl)epipodophyllotoxin-4'-deoxy-4'-phosphate By the same sequence of reactions as for Example 6, but using the derivative of formula I (R=4- hydroxyphenoxyacetyl and R'=H), described in patent FR 2,699,535-A$_1$ in Example 20, the compound is obtained in a yield of:

m.p. ~130° C. Anal. $C_{66}H_{98}N_3O_{43}P_3.6H_2O$; MW=1822.503

Calc. C43.49 H6.08 N2.31

Found C43.30 H5.88 N2.77

IR (KBr) σ (cm-1): 3429, 1763, 1508, 1199, 1084.

EXAMPLE 8

Formula I

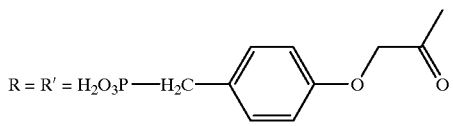

R = R' = H$_2$O$_3$P—H$_2$C—

4'-(4-phosphonomethylphenoxyacetyl)-4'-demethyl-4-O-(2,3-bis(4-phosphonomethylphenoxyacetyl)-4,6-ethylidene-β-D-glucosyl)epipodophyllotoxin 1st Stage: 4-benzyloxyphenylmethyl Diethyl Phosphonate 1 g (4.3×10$^{-3}$ mol) of 4-benzyloxybenzyl chloride are maintained at reflux for 6 h with 0.9 ml (5.15×10$^{-3}$ mol) of triethyl phosphite. The reaction medium is filtered through 150 g of SiO$_2$ and eluted with a mixture of heptane/ethyl acetate (20/80) to give, after evaporation, 1.4 g of the phosphonate derivative (yield=100%).

2nd Stage: 4-hydroxyphenylmethyl Diethyl Phosphonate

In an autoclave, 1.1 g (3.3×10$^{-3}$ mol) of the benzyloxy derivative of the 1st stage are hydrogenated under a hydrogen pressure of 7 bar in the presence of 200 mg of 10% palladium-on-charcoal in 15 ml of a mixture of ethyl acetate/ethanol (90/10) at a temperature of 80° C. for 12 h with stirring. After filtration of the catalyst, the filtrate is evaporated under reduced pressure to give 800 mg (100% yield) of the phenolic derivative.

3rd Stage: Diethyl Phosphonomethylphenoxyacetic Acid

To a THF solution (250 ml) of 2.7 g (11 mmol) of the above phenolic derivative are added 1.3 g (26 mmol) of NaH (50% dispersion) at room temperature, after which 1.8 g (13 mmol) of bromoacetic acid are introduced and the reaction medium is maintained at reflux for 8 h. The reaction medium is poured onto 1 l of ice-water and extracted with ethyl ether. The aqueous phases are acidified to pH 1.2 and extracted with ethyl acetate, dried and evaporated to give 3.1 g (94% yield) of the acetic derivative. $^1$H 200 MHz NMR (CDCl$_3$) δ 8.09 (multiplet, 1H, exchangeable) 7.16–7.26 (dd, 2H, J=8 Hz, 2 Hz, aromatic H), 6.85 (2H, d, J–8 Hz, aromatic H), 4.6 (2H, s, OCH$_2$CO$_2$H), 4.0 (4H, m, phosphonate ester OCH$_2$), 3.12 (2H, d, J=21.7 Hz, CH$_2$P), 1.23 (6H, t, J=7 Hz, phosphonate ester OCH$_2$CH$_3$).

4th Stage: Condensation of the Acid Obtained in the 3rd Stage With Etoposide

To 3 g (10.2 mmol) of the above acid obtained in the 3rd stage, dissolved in methylene chloride (15 ml) and 0.2 ml of DMF at 0° C. under nitrogen, are added dropwise 1.4 g (11.2 mmol) of oxalyl chloride and, after a consideration evolution of CO$_2$, the reaction medium is allowed to return to room temperature. The mixture is cooled again to 0° C. in order to introduce a solution containing 1 g (1.7 mmol) of etoposide and 2 g (25.5 mmol) of pyridine in methylene chloride (45 ml) dropwise. At the end of the addition, the medium is stirred for a further 4 h while returning to room temperature. After evaporation under reduced pressure, the reaction medium is taken up in toluene and evaporated and the residue is stirred with ethyl acetate and N-hydrochloric acid. After extraction, the organic phase is washed with chilled sodium bicarbonate solution and then with saturated NaCl solution, separated by settling, dried and evaporated to give a brown foam which is chromatographed on SiO$_2$ (98/2 CH$_2$Cl$_2$/MEOH eluent) and gives after evaporation a solid residue of 220 mg (10% yield), mass (FAB) m/e 1441 (M$^+$).

$^1$H NMR 200 MHz gives the characteristic peaks of these molecules: (CDCl$_3$) δ 7.20 (6H, m, arom-phosphonate H), 6.65–6.93 (6H, d, J=8.4 Hz, arom. phenoxy H) 6.75 (1H, s, H$_5$), 6.47 (1H, s, H$_8$), 6.24 (2H, s, H$_2$ and H$_6$), 5.87 (1H, s, OCH$_A$O), 5.61 (1H, s, OCH$_B$O), 5.35 (1H, t, H$_{3''}$), 5.05 (1H, t, H$_{2''}$), 3.0 (6H, d, J=21 Hz, CH$_2$ phosphonate).

5th Stage: Hydrolysis of the Phosphonic Esters 220 mg (0.16 mmol) of the phosphonic triester derivative obtained in the 4th stage are placed in CH$_3$CN (50 ml) at 0° C. under nitrogen and 0.26 ml of pyridine (3.2 mmol) are added, followed by dropwise addition of 0.49 g (3.2 mmol) of trimethylsilyl bromide. Stirring is continued for 24 h while returning to room temperature. The mixture is evaporated to dryness, the medium is taken up in N HCl, the product precipitates out and the white precipitate is filtered off and rinsed with water until neutral. The precipitate is dissolved in methanol, filtered and evaporated. The residue is taken up in water and crystallized to give 120 mg of the phosphonic derivative (57% yield).

m.p.°=190° C. Anal. $C_{56}H_{59}O_{28}P_3.5H_2O$; MW=1301.41

Calc. % C51.68 H5.34

Found % C51.91 H4.90

IR σ (KBr) 3431, 2922, 1774, 1608, 1512, 1485

$^1$H 200 MHz NMR (CD$_3$OD) δ 7.15–7.23 (6H, m, arom. methylphosphonic H), 7.04 (1H, s, H$_5$), 6.9 (2H, d, arom phenoxy H), 6.8 (2H, d, arom phenoxy H), 6.67 (2H, d, arom phenoxy H), 6.50 (1H, s, H$_8$), 6.35 (2H, s, H$_{2'}$, H$_{6'}$), 5.85 (1H, s, OCH$_A$O), 5.58 (1H, s, OCH$_B$O), 3.05 (2H, d, CH$_2$P), 2.9 (1H, dd, H$_3$), 1.3 (3H, d, H$_{8''}$).

By the same reaction as for Example 8, 4th stage or Example 25, the following compounds are prepared (route C) by triacylation on etoposide, starting with the corresponding acids A-Z-CH$_2$-CO-H:

EXAMPLE 9

Formula I

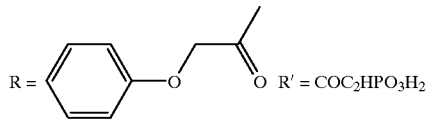

R =       R' = COC$_2$HPO$_3$H$_2$

4'-(phosphonoacetyl)-4'-demethyl-4-O-(2,3-bisphenoxy-cetyl-4,6-ethylidene-β-D-glucosyl)epipodophyllotoxin To a solution of 400 mg (2 mmol) of diethyl phosphonoacetic acid in 5 ml of CH$_2$Cl$_2$ and 3 drops of DMF under nitrogen at 0° C. are added 266 mg (2.1 mmol) of oxalyl chloride. Stirring is continued for 15 min at 0° C. and then a solution of 500 mg (0.583 mmol) of 4'-demethyl-4-O-(2,3-bisphenoxyacetyl-4,6-ethylidene-β-D-glucosyl)epipodophyllotoxin in 5 ml of CH$_2$Cl$_2$ and 184 mg (188 μl, 23 mmol) of pyridine are introduced into the reaction medium at 0° C. The contact is maintained for 2.5 h and the reaction medium is then poured onto N HCl. The organic

13 phase is separated out after settling, washed with NaCl solution, dried and evaporated. The residue is crystallized from ethyl ether to give a white precipitate (450 mg, 75% yield). 320 mg (0.31 mmol) of this derivative are placed, with stirring, in 10 ml of acetonitrile in the presence of 470 mg (0.4 ml, 0.31 mmol) of trimethylsilyl bromide and 240 mg (0.25 ml, 0.31 mmol) of pyridine, at room temperature for 6 h.

After evaporation, the residue is taken up in N HCl to give a white solid which is filtered off, washed with water and dried. 180 mg (57% yield) of the phosphonic derivative are obtained.

m.p.°~140° C. Anal. $C_{47}H_{47}O_{21}P \cdot 2H_2O$ (MW=1014.996)

Calc. % C55.61 H5.06

Found % C55.87 H4.80

IR σ(KBr) 3431, 1774, 1601, 1487

$^1$H 200 MHz NMR (CDCl$_3$) δ 7.16–7.27 (4H, m, m-arom, H), 6.68–6.95 (7H, m, o.p.-arom H, $H_5$), 6.44 (1H, s, $H_8$), 6.24 (2H, s, $H_2'$–$H_6'$), 5.82 (1H, s, $OCH_AO$), 5.56 (1H, s, $OCH_BO$), 5.32 (1H, dd, $H_3''$), 5.02 (1H, t, $H_2''$), 3.2 (m, 3H, $CH_2P$, $H_2$), 1.32 (d, 3H, J~4.4 Hz, $H_8''$).

EXAMPLE 10

Formula I

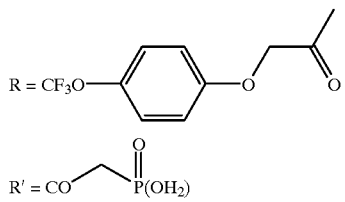

4'-(phosphonoacetyl)-4'-demethyl-4-O-(2,3-bis(4-trifluoromethoxyphenoxyacetayl)-4,6-ethylidene-β-D-glucosyl)epipodophyllotoxin. N-methylglucamine Salt This derivative is obtained by the same method as for Example 9, but starting with the derivative of formula I for which R=4-trifluoromethoxyphenoxyacetyl and R'=H.

Preparation of the N-methylglucamine salt: 810 mg (0.7 mmol) of the phosphonic derivative in ethanol (15 ml) and 0.5 ml of acetone are introduced, after which 14.1 ml of a 0.1N solution of N-methylglucamine (1.41 mmol) in ethanol are introduced dropwise with stirring. Stirring is continued for 1 h. The reaction medium is evaporated and the residue is taken up in water and then filtered (0.45µ filter). The aqueous solution is lyophilized and the residue is taken up in isopropanol, crystallized, filtered and dried to give 700 mg (65% yield) of N-methylglucamine salt.

m.p.°=120° C. Anal. $C_{63}H_{79}N_2F_6O_{33}P \cdot 3.5H_2O$; MW=1600.47

Calc. % C47.28 H5.42 N1.75

Found % C46.95 H5.47 N2.07

IR σ (KBr) 3426, 1774, 1601, 1500, 1487

14

EXAMPLE 11

Formula I

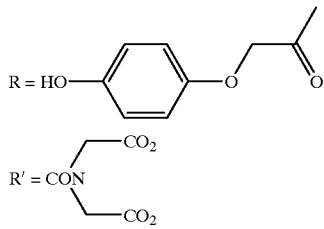

4'-(dicarboxymethylaminocarbonyl)-4'-demethyl-4-O-(2,3-bis(p-hydroxyphenoxyacetyl)-4,6-ethylidene-β-D-glucosyl)epipodophyllotoxin 1st Stage: Preparation of the Benzyl Diester of Aminodiacetic Acid To a solution of 10 g (49.6 mmol) of glycine benzylester hydrochloride in 200 ml of $CH_3CN$ are added 13.7 g (99 mmol) of $K_2CO_3$, and 8 ml (49.6 mmol) of benzyl bromoacetate dropwise. The medium is stirred at room temperature for 2 days. 200 ml of water are added and the medium is acidified to pH 2–3 with concentrated HCl and then extracted with ethyl acetate in order to obtain 12 g (80% yield) of the diester used in the following step.

2nd Stage: Preparation of the Carbamate

A solution of phosgene (0.79 ml, 1.5 mmol) in toluene at 1.93M is introduced into 50 ml of acetonitrile and then cooled to −10° C. under a nitrogen atmosphere. 820 mg (0.76 mmol) of 4'-demethyl-4-O-(2,3-bis(p-benzyloxyphenoxyacetyl)-4,6-ethylidene-β-D-glucosyl) epipodophyllotoxin in 13 ml of acetonitrile and 0.24 g of diisopropylethylamine are introduced dropwise. The reaction medium is stirred for 2 h at −10° C., after which 0.24 g of the benzyl diester of aminodiacetic acid, obtained in the 1st stage, in 6 ml of acetonitrile is added at −5° C. Stirring is continued for 6 h. The reaction medium is next evaporated and then filtered through $SiO_2$ and eluted with a solvent gradient: 70/30 and then 60/40 and finally 50/50 petroleum ether/ethyl acetate in order to obtain 700 mg (65% yield) of the benzyl diester derivative.

3rd Stage: Hydro-Enolysis of the Benzyl Functions 700 mg of the derivative obtained in the 2nd stage are placed in solution in a mixture of 13 ml of ethyl acetate and 3 ml of ethanol, in an autoclave under a hydrogen atmosphere in the presence of 70 mg of 10% palladium-on-charcoal. Stirring is continued for 24 h and the reaction medium is then filtered and evaporated. The residue is crystallized from isopropyl ether in order to obtain 480 mg (92% yield) of the diacid derivative.

m.p.°~150° C. Anal. $C_{50}H_{49}NO_{24}$ $_{MW=}$1047.94

Calc. % C57.31 H4.71 N1.34

Found % C57.07 H4.96 N1.13

IR σ (KBr) 3433, 1768, 1603, 1512, 1485, 1460, 1236, 1199

$^1$H 200 MHz NMR (DMSO) δ 9.03 and 8.98 (2H, 2s, $CO_2H$, exchangeable), 6.45–6.67 (10H, m, $H_5$, $H_8$, ArH), 6.21 (2H, s, $H_2'$, $H_6'$), 6.0 (1H, s, $OCH_AO$), 5.79 (1H, s, $OCH_BO$), 5.32 (2H, m, $H_2''$ and $H_3''$), 3.39 (s, N-$CH_2$-$CO_2H$), 1.20 (3H, d, $H_8''$).

By the same method as in Example 11, 2nd stage, but using the corresponding intermediate compounds of formula I (R'=H), the following novel derivatives were prepared.

EXAMPLE 12

Formula I

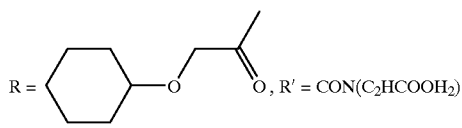

4'-(dicarboxymethylaminocarbonyl)-4'-demethyl-4-O-(2,3-biscyclohexyloxyacetyl-4,6-ethylidene-β-D-glucosyl)epipodophyllotoxin Yield=98% m.p.°=170° C. Anal. $C_{50}H_{61}NO_{22}$ MW=1028.037

EXAMPLE 13

Formula I

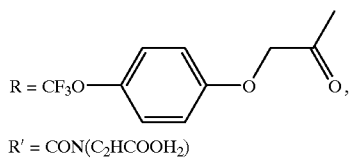

4'-(dicarboxymethylaminocarbonyl)-4'-demethyl-4-O-(2,3-bis(p-trifluoromethoxyphenoxyacetyl)-4,6-ethylidene-β-D-glucosyl)epipodophyllotoxin Yield=87% m.p.~150° C. Anal. $C_{52}N_{47}NO_{24}F_6$ MW=1183.94

Calc. % C52.75 H4.00 N1.20

Found % C52.64 H4.10 N1.30

EXAMPLE 14

Formula I

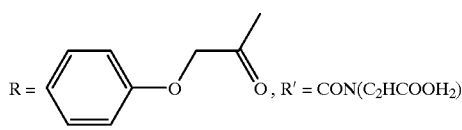

4'-(dicarboxymethylaminocarbonyl)-4'-demethyl-4-O-(2,3-bisphenoxyacetyl-4,6-ethylidene-β-D-glucosyl)epipodophyllotoxin Yield=25% m.p.~170° C. Anal. $C_{50}H_{49}N\ O_{22}\cdot H_2O$ MW=1033.955

Calc. % C58.08 H4.97 N1.35

Found % C58.43 H5.05 N1.28

EXAMPLE 15

Formula I

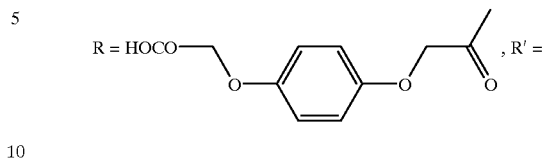

4'-demethyl-4-O-(2,3-bis-(4-carboxymethoxyphenoxyacetyl)-4,6-ethylidene-β-D-glucosyl)epipodophyllotoxin, N-methylglucamine Salt 1st Stage: Benzyl 4-hydroxyphenoxyacetate To a suspension of 10 g (59 mmol) of p-hydroxyphenoxyacetic acid in 100 ml of $CH_2Cl_2$ at 0° C. under a nitrogen atmosphere are added 0.2 ml of DMF followed by dropwise addition of 9 g of oxalyl chloride (71 mmol). Stirring is continued for 12 h at room temperature, then 7.7 g (71 mmol) of benzyl alcohol are introduced and stirring is continued for 8 h at room temperature. The reaction medium is poured onto chilled ammoniacal solution and is extracted with methylene chloride. The organic phase is washed with N HCl, separated by settling, dried and evaporated. The residue is filtered through 150 g of $SiO_2$ and eluted with a heptane/ethyl acetate mixture (75/25) to give 3.8 g (25% yield) of a white solid.

$^1$H 200 MHz NMR ($CDCl_3$) δ 7.36 (5H, s, Ar), 6.75 (4H, d, ArOH), 5.24 (2H, s, $CH_2$ Ar), 4.61 (2H, s, $OCH_2CO$).

2nd Stage: 4-benzyloxycarbonylmethoxyphenoxyacetic Acid 3.8 g of the phenol obtained in the 1st stage are maintained in refluxing THF (200 ml) in the presence of 1.3 g of NaH (60% dispersion) and 2 g of bromoacetic acid for 48 h. The reaction medium is then poured onto ice and extracted with isopropyl ether and then with ethyl acetate. The aqueous phase is acidified and extracted with $CH_2Cl_2$ to [lacuna] 2.8 g (60% yield) of a cream-colored solid.

$^1$H 200 MHz NMR ($CDCl_3$) δ 7.35 (5H, s, Ar), 6.78 (4H, s, ArO), 5.15 (2H, s, $CH_2Ar$), 4.55 (2H, s, $OCH_2$ester), 4.45 (2H, s, $OCH_2$ acid)

3rd Stage: Coupling of the Acid of the 2nd Stage with 4'-benzyloxycarbonyletoposide To 1.75 g (5.5 mmol) of the acid of the 2nd stage dissolved in 40 ml of $CH_2Cl_2$ with 0.2 ml of DMF are added dropwise at 0° C. under a nitrogen atmosphere 770 mg (6.1 mmol) of oxalyl chloride. Stirring is continued for 2 h at room temperature. After cooling to 0° C., a solution of 1 g (1.38 mmol) of 4'-benzyloxycarbonyletoposide and 1.1 g (1.38 mmol) of pyridine in 10 ml of $CH_2Cl_2$ is then added. After stirring for 3 h at room temperature, the reaction medium is concentrated, taken up in ethyl acetate and washed with water, then with chilled sodium bicarbonate solution, after again washing with N HCl and then with saturated NaCl solution, the organic phase is separated out after settling, dried and evaporated to give 800 mg (66% yield) which are directly hydrogenolysed in the following stage (TLC $SiO_2$ 20/80 heptane/EtOAc Rf=0.9)

4th Stage: Hydrogenolysis 800 mg (0.6 mmol) of derivative obtained in the 3rd stage are placed under a hydrogen atmosphere at atmospheric pressure in 15 ml of ethyl acetate and 5 ml of ethanol in the presence of 100 mg of palladium-on-charcoal, with vigorous stirring for one hour. The catalyst is filtered off and the filtrate is evaporated. The residue is taken up in acetone, filtered again and evaporated to give the debenzylated derivative quantitatively (650 mg). This derivative is converted into the N-methylglucamine salt by addition of 2 equivalents of a 0.1M solution of N-methylglucamine in an EtOH, H$_2$O-acetone mixture. After stirring for 1 h, the solution is evaporated, taken up in H$_2$O, filtered through a 0.45μ filter and lyophilized, and 700 mg of the carboxylic derivative are thus obtained.

m.p.~130° C. Anal. C$_{63}$H$_{82}$N$_2$O$_{33}$.6H$_2$O; MW=1503.422
Calc. % C50.33 H6.30 N1.86
Found % C49.89 H5.93 N2.19
IR σ (KBr) 3427, 1772, 1618, 1508, 1425, 1205, 1087
$^1$H 200 MHz NMR (DM50) δ 7.04 (1H, s, H$_5$), 6.59–6.70 (8H, m, OArO), 6.47 (1H, s, H$_8$), 6.13 (2H, s, H$_{2'}$ and H$_{6'}$), 5.96 (1H, s, OCH$_A$O), 5.73 (1H, s, OCH$_B$O), 5.33 (2H, m, H$_{2''}$ and H$_{3''}$), 2.46 (6H, s, NCH$_3$), 1.20 (3H, d, J=4 Hz, H$_{8''}$).

By the same sequence of reactions as in Example 15, but using the appropriate reagents, the derivatives of general formula I (R'=H) are obtained:

EXAMPLE 16

Formula I

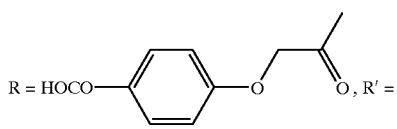

4'-demethyl-4-O-(2,3-bis(4-carboxyphenoxyacetyl)-4,6-ethylidene-β-D-glucosyl)epipodophyllotoxin Using 4-benzyloxycarbonylphenoxyacetic acid, according to the process of Example 15, the carboxylic derivative is obtained in a yield of 45%.

m.p.~170° C. Anal. C$_{47}$H$_{44}$O$_{21}$.1.3H$_2$O MW=968.469
Calc. % C58.28 H4.81
Found % C58.19 H4.85
N-Methylglucamine salt
F=138° C. Anal. C$_{61}$H$_{78}$N$_2$O$_{31}$.5H$_2$O MW=1425.355
Calc. % C51.40 H6.22 N1.97
Found % C51.27 H5.85 N2.19

EXAMPLE 17

Formula I

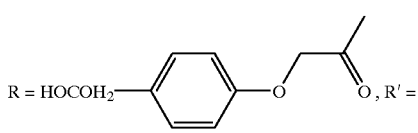

4'-demethyl-4-O-(2,3-bis(4-carboxyphenoxyacetyl)-4,6-ethylidene-β-D-glucosyl)epipodophyllotoxin Using 4-benzyloxycarbonylmethylphenoxyacetic acid, according to Example 15, the acetic derivative is obtained (66% yield).

m.p.~150° C. Anal. C$_{49}$H$_{48}$O$_{21}$.2H$_2$O MW=1008.932
Calc. % C58.33 H5.19
Found % C57.74 H4.85
Mass spectrography (FAB) m/e 972 (M$^+$)

By the method of Example 15, 3rd stage only, the following derivatives are prepared:

EXAMPLE 18

Formula I

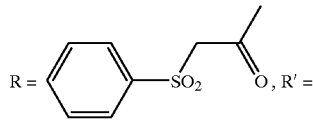

4'-demethyl-4-O-(2,3-bis(phenylsulfonylacetyl)-β-D-glucosyl)epipodophyllotoxin

Yield=92%
m.p.=248° C. Anal. C$_{45}$H$_{44}$O$_{19}$S$_2$ MW=976.790
Calc. % C56.72 H4.65
Found % C56.40 H4.66

EXAMPLE 19

Formula I

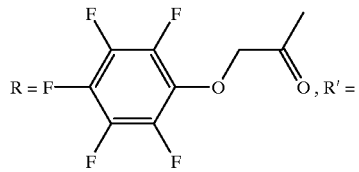

4'-demethyl-4-O-(2,3-bis(4-pentafluorophenoxyacetyl)-β-D-glucosyl) epipodophyllotoxin Yield=75% Anal. C$_{45}$H$_{34}$O$_{17}$F$_{10}$ MW=1036.75
C H
Calc. % 52.13 3.30
Found % 51.88 3.25

EXAMPLE 20

Formula I

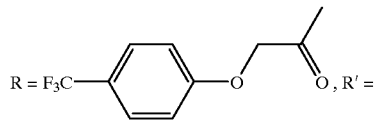

4'-demethyl-4-O-(2,3-bis(4-trifluoromethylphenoxyacetyl)-β-D-glucosyl) epipodophyllotoxin Yield=53% Anal. C$_{47}$H$_{42}$O$_{17}$F$_6$ MW=992.820
C H
Calc. % 56.86 4.26
Found % 56.78 4.22

EXAMPLE 21

Formula I

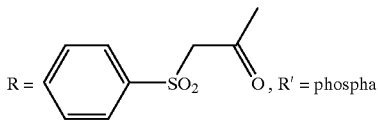

R = phenylsulfonyl group, R' = phospha

4'-demethyl-4'-deoxy-4'-phosphate-4-O-(2,3-bis(phenylsulfonylacetyl)-4,6-ethylidene-β-D-glucosyl)epipodophyllotoxin Bis(N-methylglucamine) Salt Using the method of Example 1, but with the compound of Example 18, the phosphate derivative is obtained in the form of the N-methylglucamine salt.

Yield=60% Anal. $C_{59}H_{79}N_2O_{32}PS_2.3.8H_2O$

F~148° C.

MW=1492.85

C H N

Calc. % 49.79 5.59 1.97

Found % 47.47 5.85 1.88

EXAMPLE 22

Formula I

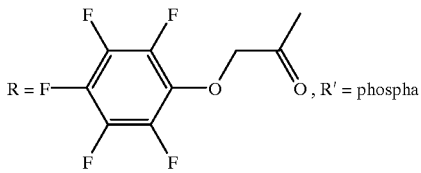

R = F, R' = phospha

4'-demethyl-4'-deoxy-4'-phosphate-4-O-(2,3-bis(2,3,4,5,6-pentafluorophenoxyacetyl)-4,6-ethylidene-β-D-glucosyl)epipodophyllotoxin Bis(N-methylglucamine) Salt Using the method of Example 1, but with the compound of Example 19, the phosphate derivative is obtained in the form of N-methylglucamine salt.

Yield=78% m.p.~140° C. Anal. $C_{59}H_{69}F_{10}N_2O_{30}P.3.5H_2O$; MW=1507.147

C H N

Calc. % 45.11 4.88 1.78

Found % 45.34 4.67 1.82

EXAMPLE 23

Formula I

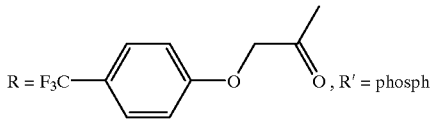

R = F$_3$C, R' = phosph

4'-demethyl-4'-deoxy-4'-phosphate-4-O-(2,3-bis(4-trifluoromethylphenoxyacetyl)-4,6-ethylidene-β-D-glucosyl)epipodophyllotoxin Bis(N-methylglucamine) Salt Using the method of Example 1, but with the compound obtained in Example 20, the phosphate derivative is obtained in the form of the N-methylglucamine.

Yield=33% m.p.=120° C. Anal. $C_{61}H_{77}N_2O_{30}F_6P.4.15H_2O$; MW=1538.170

C H N

Calc. % 47.63 5.59 1.82

Found % 47.16 5.15 1.84

EXAMPLE 24

Formula I

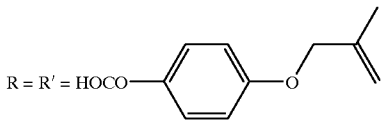

R = R' = HOCO

Route C

4'-demethyl-4'-(4-carboxyphenoxyacetyl)-4-O-(2,3-bis(4-carboxyphenoxyacetyl)-4,6-ethylidene-β-D-glucosyl)epipodophyllotoxin Glucamine Salt

1st Stage: Condensation of 4-benzyloxycarbonylphenoxyacetic Acid with Etoposide To a solution of 4.9 g (17 mmol) of 4-benzyloxycarbonylphenoxyacetic acid in 100 ml of CH$_2$Cl$_2$ and 0.2 ml of DMF are added dropwise at 0° C. under nitrogen 2.4 g (18.7 mmol) of oxalyl chloride, and, after stirring for 2 h at room temperature, 2 g (3.4 mmol) of etoposide dissolved in 15 ml of CH$_2$Cl$_2$ and 3.2 g (41 mmol) of pyridine are introduced dropwise at 0° C. into this solution. After warming to room temperature over 3 hours, the reaction medium is poured onto N HCl and then extracted with CH$_2$Cl$_2$ and washed with NaHCO$_3$ solution and saturated NaCl successively in order to obtain, after evaporation, a crude product which is chromatographed on SiO$_2$ by elution in a heptane/EtOAc mixture (60/40). 1.8 g (38% yield) of trisubstituted derivative are obtained, which product is used directly in the following step.

2nd Stage: Hydrogenolysis 1.5 g (1.07 mmol) of the above benzyltriester is hydrogenolysed in the presence of hydrogen at atmospheric pressure in a mixture of EtOH (15 ml) and EtOAc (60 ml) with 300 mg of 10% palladium-on-charcoal, with vigorous stirring for 8 h at room temperature. The catalyst is filtered off and the evaporated filtrate is chromatographed on $SiO_2$ and eluted with a $CH_2Cl_2$/MeOH mixture (96/4) in order to obtain a white solid (600 mg, 50% yield). The glucamine salt prepared directly, is obtained by placing 3 equivalents of an aqueous 0.1M solution of N-methylglucamine in an EtOH/$H_2O$ mixture (80/20), and this solution is added to the solution of the triacid in acetone. A gummy precipitate is obtained, and the medium is evaporated and then taken up in $H_2O$ and filtered through a $0.45\mu$ filter. The filtrate is then lyophilized in order to obtain the glucamine salt.

Yield=50% m.p.~135° C. Anal. $C_{77}H_{101}N_3O_4.7H_2O$ MW=1836.103

C H N

Calc. % 50.37 6.32 2.29

Found % 49.99 5.77 2.43

IR ν (KBr) 3404, 1772, 1604, 1545, 1385, 1086.

$^1$H 200 MHz NMR (DMSO), 7.77–7.85 (6H, m, Ar), 7.1 (1H, s, $H_5$), 6.89, 6.79, 6.64 (6H, d, J=8.7 Hz, ArO), 7.08 (1H, s, $H_5$), 6.46 (1H, s, $H_8$), 6.26 (2H, s, $H_{2'}$ and $H_{6'}$), 6.13 (1H, s, $OCH_AO$), 5.95 (1H, s, $OCH_BO$), 2.42 (9H, s, N—$CH_3$), 1.20 (3H, d, J=4.9 Hz, $H_{8''}$).

EXAMPLE 25

Formula I

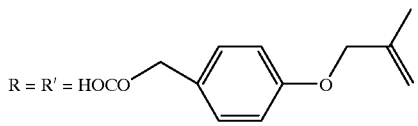

4'-demethyl-4'-carboxymethylphenoxyacetyl-4-O-(2,
3-bis(4-carboxymethylphenoxyacetyl)-4,6-
ethylidene-β-D-glucosyl)epipodophyllotoxin This derivative is obtained by the same method as for Example 24, but using benzyloxycarbonylmethylphenoxyacetic acid.

Yield=20% m.p.~150° C. Anal. $C_{59}H_{56}O_{25}.1.4H_2O$; MW=1190.703

C H

Calc. % 59.63 4.81

Found % 59.19 4.84

EXAMPLE 26

Formula I

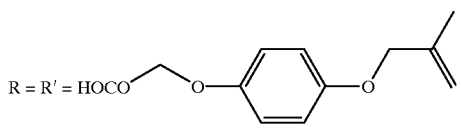

4'-demethyl-4'-carboxymethoxyphenoxyacetyl-4-O-
(2,3-bis(4-carboxymethoxyphenoxyacetyl)-4,6-
ethylidene-β-D-glucosyl)epipodophyllotoxin N-methylglucamine Salt This derivative is obtained by the same method as for Example 24, but using benzyloxycarbonylmethoxyphenoxyacetic acid.

Yield=84% m.p.~110° C. Anal. $C_{80}H_{107}N_3O_{43}.6.3H_2O$ MW=1912.036

C H N

Calc. % 50.25 6.30 2.20

Found % 50.13 6.17 2.56

EXAMPLE 27

Formula I

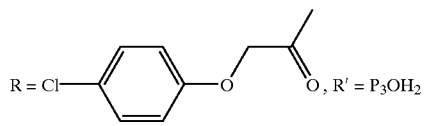

4'-demethyl-4'-deoxy-4'-phosphate-4-O-(2,3-bis(4-
chlorophenoxyacetyl)-4,6-ethylidene-β-D-glucosyl)
epipodophyllotoxin 1st Stage: 4'-(3-quinuclidinylaminocarbonyl)
etoposide Formula V $R_4$=COHN 3-quinuclidinyl To a 1.93M solution of phosgene in acetonitrile (8.8 ml, 16.9 mmol) cooled to 0° C. under nitrogen is added dropwise a solution of etoposide (5 g, 8.49 mmol) in 200 ml of $CH_3CN$ and 2.74 g (21.2 mmol) of N,N-diisopropylethylamine over 10 min, after which 1.07 g (8.49 mmol) of 3-aminoquinuclidine dissolved in 20 ml of $CH_3CN$ are introduced. The medium is stirred for 24 h. After evaporation, the residue is chromatographed on $SiO_2$ with a mixture of solvents: $CHCl_3$/MeOH/$NH_4OH$ (93/7/0.7) and then (90/10/1). 1.67 g (26% yield) of carbamate product V, which is homogeneous on TLC, is obtained, and is immediately reacted in the 2nd stage.

2nd Stage: Condensation with p-
chlorophenoxyacetic Acid

To a solution of 1.68 g (8.98 mmol) of p-chlorophenoxyacetic acid in chloroform (40 ml) and 0.5 ml of DMF at 0° C. under a nitrogen atmosphere are introduced dropwise 1.25 g (9.88 mmol) of oxalyl chloride. Stirring is continued for 1 h. This solution is then added dropwise to the solution of the etoposide derivative obtained in the 1st stage (1.66 g, 2.24 mmol) in 60 ml of chloroform and 1.77 g of pyridine at 0° C. This new solution is stirred for 5 h while returning to room temperature. The reaction medium is then poured onto N HCl (100 ml), separated by settling and then washed with saturated NaCl solution, dried and evaporated to give an oil which is chromatographed on silica. Elution with a mixture of CHCl3/MeOH/$NH_4OH$ (95/5/0.5) gives 1.97 (80% yield) of the derivative in the title of Example 26. The hydrochloride is formed therefrom (by addition of a saturated ether solution of hydrochloric acid gas to the solution of the base in acetone. After stirring for 10 min, the precipitate obtained is filtered off slowly, washed with ether and dried (50% yield).

m.p.~180° C. Anal. $C_{53}H_{54}Cl_2N_2O_{18}.HCl.2H_2O$ MW=1150.422

C H N

Calc. % 55.33 5.08 2.43

Found % 55.74 4.96 2.61

Mass spectrum (FAB) m/e 1077 (M$^+$)

3rd Stage: Hydrolysis

To a solution in 70 ml of acetone of 1.08 g of the derivative of the 2nd stage are introduced 30 ml of saturated NaHCO$_3$ solution. The medium is stirred for 2 days, the acetone is evaporated off and the medium is acidified with concentrated HCl to pH 2 and is then extracted with methylene chloride. Chromatography on SiO$_3$ (97/3 CH$_3$Cl$_2$/MeOH elution) gives the derivative of the title of Example 27. A further chromatography on SiO$_2$ (1/1 petroleum ether/EtOAc elution) gives, after evaporation, a residue which crystallizes from isopropyl ether (200 mg, yield=21%).

m.p.~125° C. Anal. C$_{45}$H$_{42}$Cl$_2$O$_{17}$ MW=925.730

C H

Calc. % 58.38 4.57

Found % 58.63 4.69

Mass spectrum (FAB) m/e 924 (M+−1)

IR ν (KBr) 3548, 1774, 1616, 1491.

$^1$H 200 MHz NMR (CDCl$_3$) δ 7.15–7.22 (4H, m, Ar), 6.75 (1H, s, H$_5$), 6.77 (2H, d, J=8.8 Hz, ArO), 6.64 (2H, d, J=8.8 Hz, ArO), 6.51 (1H, s, H$_8$), 6.22 (2H, s, H$_2$' and H$_{6'}$), 5.91 (1H, s, OCH$_A$O), 5.71 (1H, s, OCH$_B$O), 5.33 (1H, t, J=9 Hz, H$_{3''}$), 5.02 (1H, t, J=7.8 Hz, H$_{2''}$), 4.91 (1H, d, J=7.8 Hz, H$_{1''}$), 4.83 (1H, d, J=3.2 Hz, H$_4$), 4.69 (1H, q, H$_{7''}$), 3.1 (1H, dd, H$_2$), 2.9 (1H, m, H$_3$), 1.34 (3H, d, J=5 Hz, H$_{8''}$).

Preparation of the Phosphate

This derivate is obtained according to the procedure of Example 1, but using the derivative obtained in the 3rd stage.

N-Methylglucamine Salt

Yield=70% m.p.~140° C. Anal. C$_{59}$H$_{77}$Cl$_2$N$_2$O$_{30}$P.6H$_2$O MW=1461.49

C H N

Calc. % 48.49 5.8 1.90

Found % 48.78 5.55 1.88

EXAMPLE 28

Formula I

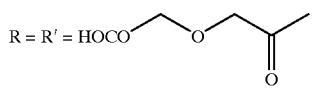

R = R' = HOCO

4'-demethyl-4'-carboxymethoxyacetyl-4-O-(2,3-bis(carboxymethoxyacetyl-4,6-ethylidene-β-D-glucosyl)epipodophyllotoxin This derivate is prepared according to the method of Example 24, 1st and 2nd stage, in which benzyloxycarbonylmethoxyacetic acid is used instead of the 4-benzyloxycarbonylphenoxyacetic acid, to give successive yields of 77% and 75%.

m.p.=138° C. Anal. C$_{41}$H$_{44}$O$_{25}$.H$_2$O MW=954.805

C H

Calc. % 51.57 4.85

Found % 51.22 4.72

Mass spectrum (FAB) m/e 959 (M$^+$+Na)

EXAMPLE 29

Formula I

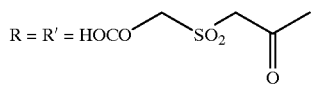

R = R' = HOCO SO$_2$

4'-demethyl-4'-carboxymethylsulfonylacetyl-4-O-(2,3-biscarboxymethylsulfonylacetyl-4,6-ethylidene-β-D-glucosyl)epipodophyllotoxin This derivate is prepared as for the above, according to the method of Example 24, 1st and 2nd stages, using benzyloxycarbonylmethylsulfonylacetic acid, in successive yields of 55% and 90%.

m.p.~165° C. Anal. C$_{41}$H$_{44}$O$_{28}$S$_3$.H$_2$O MW=1098.98

C H

Calc. % 44.81 4.22

Found % 44.94 4.34

Mass spectrum (FAB) m/e 1103 (M$^+$+Na)

EXAMPLE 30

Formula I

R = HOCOC$_2$OCH$_2$CO, R' =

4'-demethyl-4-O-(2,3-biscarboxymethoxyacetyl-4,6-ethylidene-β-D-glucosyl)epipodophyllotoxin This derivative is obtained by the method described for Example 15, 3rd and 4th stages, but using benzyloxycarbonylmethoxyacetic acid instead of benzyloxycarbonylmethoxyphenoxyacetic acid. The successive yields are 42% and 71%.

m.p.~192° C. Anal. C$_{37}$H$_{40}$O$_{21}$.0.2H$_2$O MW=824.32

C H

Calc. % 54.59 5.20

Found % 54.81 5.23

EXAMPLE 31

Formula I

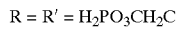

R = R' = H$_2$PO$_3$CH$_2$C

4'-demethyl-4'-phosphonoacetyl-4-O-(2,3-bisphosphonoacetyl-4,6-ethylidene-β-D-glucosyl)epipodophyllotoxin This derivative is obtained in that identical manner to the method of Example 24, 1st and 2nd stages, but using dibenzylphosphonoacetic acid (Tet. Let. 1974, No. 9, 711). The changes relative to Example 24 are as follows: the first stage is carried out at 0° C., with a return to room temperature over 18 h; the hydrogenolysis in the second stage is carried out in the solvent: 25 ml THF and 50 ml EtOH, and the reaction is carried out at 0° C. for 4 h. The yields are successively 34% and 83%.

m.p.~184° C. Anal. C$_{35}$H$_{41}$O$_{25}$P$_3$.4H$_2$O MW=1026.58

C H H$_2$O

Calc. % 40.94 4.81 7.02

Found % 40.95 4.38 7.54

Mass spectrum (FAB) m/e 955 (M$^+$+1)

EXAMPLE 32

Formula I

R = H$_2$O$_3$PCH$_2$CO, R' =

4'-demethyl-4-O-(2,3-bisphosphonoacetyl-4,6-ethylidene-β-D-glucosyl)epipodophyllotoxin This derivative is obtained in an identical manner to the method of Example 15, 3rd and 4th stages, but using dibenzylphosphonoacetic acid, already used for Example 31.

The hydrogenolysis stage is carried out using a solvent mixture: THF/EtOH (30/70) at 0° C. for 4 h. The derivative is thus obtained in an overall yield of 45%.

m.p.~168° C. Anal. C$_{33}$H$_{38}$O$_{21}$P$_2$ MW=832.606

Mass spectrum (FAB) m/e 833 (M$^+$+1).

The following compounds according to the invention were also prepared:

4'-demethyl-4'-deoxy, 4'-phosphate-4-O-(2,3-bis(4-cyanophenoxyacetyl)-4,6-ethylidene-β-D-glucosyl)epipodophyllotoxin N-methylglucamine Salt m.p.~205° C. Anal. C$_{47}$H$_{43}$N$_2$O$_{20}$P.6H$_2$O=1112.93

C H N

Calc. % 51.56 5.06 2.56

Found % 51.11 4.27 2.31

4'-demethyl-4'-deoxy, 4'-phosphate-4-O-(2,3-bis(4-nitrophenoxyacetyl)-4,6-ethylidene-β-D-glucosyl)epipodophyllotoxin N-methylglucamine Salt m.p.~190° C. Anal. C$_{45}$H$_{43}$N$_2$O$_{24}$P.4H$_2$O=10.98.88

C H N

Calc. % 49.18 4.68 2.55

Found % 49.38 4.25 2.46

4'-demethyl-4'-deoxy, 4'-phosphate-4-O-(2,3-bis(4-methylphenoxyacetyl)-4,6-ethylidene-β-D-glucosyl)epipodophyllotoxin m.p.~190° C. Anal. C$_{47}$H$_{49}$N$_2$O$_{20}$P.1.25H$_2$O=987.378

C H

Calc. % 57.12 5.21

Found % 56.6 5.04

4'-demethyl-4-O-(2,3-bis(4-phosphonooxyphenoxyacetyl)-4,6-ethylidene-β-D-glucosyl)epipodophyllotoxin N-methylglucamine salt m.p.~145–150° C. Anal. C$_{59}$H$_{80}$N$_2$O$_{35}$P$_2$.1.5H$_2$O=1466.240

C H N

Calc. % 48.33 5.71 1.91

Found % 48.46 5.93 2.09

4'-demethyl-4'-deoxy-4'-phosphate-4-O-(2,3-bis(4-hydroxyphenoxyacetyl)-4,6-ethylidene-β-D-glucosyl)epipodophyllotoxin N-methylglucamine Salt m.p.~145° C. Anal. C$_{59}$H$_{79}$N$_2$O$_{32}$P.H$_2$O=1377.26

C H N

Calc. % 51.45 5.93 2.03

Found % 51.44 6.17 2.04

What is claimed is:

1. A compound of formula I

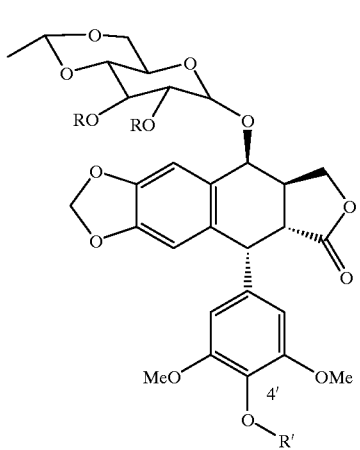

wherein R is an acyl group of the formula

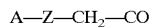

wherein A is substituted or unsubstituted phenyl, benzyl, napthyl or heteroaryl;

wherein Z is selected from the group consisting of oxygen, sulfur, an SO$_2$ group, and a linear or branched C$_1$–C$_4$ alkylene, said substituted aryl substituted with up to five substituents, each independently selected from the group consisting of halogens, linear or cyclic C$_1$–C$_6$ alkoxy, C$_1$–C$_6$ alkyl, methylenedioxy, OCF$_3$, CF$_3$, NO$_2$, CN, OCH$_2$Aryl, OH, OPO$_3$H$_2$, CH$_2$OP$_3$H$_2$, PO$_3$H$_2$, OCH$_2$CO$_2$H, COOH, CH$_2$COOH, COCH$_3$ and CHO groups; and R' is selected from the group consisting of carbamates of the formula —CO—N—(R$_1$R$_2$) where N(R$_1$R$_2$) represents aminodiacetic groups, polycyclic amines, H$_2$O$_3$P—CH$_2$—CO, C(O)CH$_2$OCH$_2$CO$_2$H, C(O)CH$_2$SO$_2$CH$_2$COOH, and phosphate monoesters;

or a therapeutically acceptable salt thereof.

2. A compound of formula I

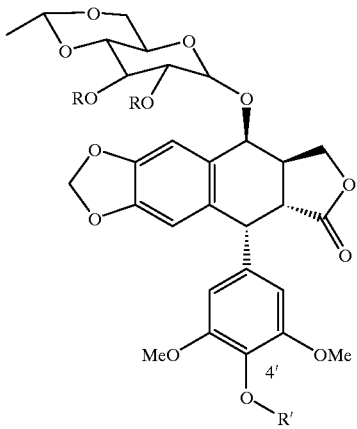

wherein R is an acyl group of the formula

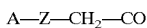

A—Z—CH₂—CO wherein A is substituted or unsubstituted phenyl, benzyl, naphthyl or heteroaryl;
wherein Z is selected from the group consisting of oxygen, sulfur, an $SO_2$ group, and a linear or branched $C_1$–$C_4$ alkylene,
said substituted aryl substituted with up to five substituents, each independently selected from the group consisting of halogens, linear or cyclic $C_1$–$C_6$ alkoxy, $C_1$–$C_6$ alkyl, methylenedioxy, $OCF_3$, $CF_3$, $NO_2$, CN, $OCH_2$Aryl, OH, $OPO_3H_2$, $CH_2PO_3H_2$, $PO_3H_2$, $OCH_2CO_2H$, COOH, $CH_2COOH$, $COCH_3$ and CHO groups; and,
R' is a phosphate monoester;
or a therapeutically acceptable salt thereof.

3. A compound of claim 2 selected from the group consisting of 4'-demethyl-4'-deoxy-4'-phosphate-4-O-(2,3-bis(4-trifluoromethylphenoxyacetyl)-4,6-ethylidene-β-D-glucosyl)epipodophyllotoxin, 4'-demethyl-4'-deoxy-4'-phosphate-4-O-(2,3-bis(4-chlorophenoxyacetyl)-4,6-ethylidene-β-D-glucosyl)epipodophyllotoxin, 4'-demethyl-4-O-(2,3-bis-(4-trifluoromethoxyphenoxyacetyl)-4,6-ethylidene-β-D-glucosyl)epipodophyllotoxin-4'-deoxy-4'-phosphate, 4'-demethyl-4'-deoxy-4'-phosphate-4-O-(2,3-bis(4-methylphenoxyacetyl)-4,6-ethylidene-β-D-glucosyl) epipodophyllotoxin, 4'-demethyl-4'-deoxy-4'-phosphate-4-O-(2,3-bis-(2,3,4,5,6-pentafluorophenoxyacetyl)-4,6-ethylidene-β-D-glucosyl)epipodophyllotoxin and therapeutically acceptable salts thereof.

4. A compound according to claim 1 wherein R' represents a phosphate monoester group ($PO_3H_2$), a carbamate group $CONR_1R_2$ where $NR_1R_2$ represents an aminodiacetic group or a 3-aminoquinuclidine group or a phosphonoacetic group, or salts thereof with therapeutically acceptable and water-soluble inorganic acids or bases.

5. A compound according to claim 1 wherein R is selected from the group consisting of: phenoxyacetyl, 3,4-methylenedioxyphenoxyacetyl, 4-methoxyphenoxyacetyl, 4-hydroxyphenoxyacetyl, 4-phosphonooxyphenoxyacetyl, 4-carboxymethylphenoxyacetyl, 4-carboxymethoxyphenoxyacetyl, 4-carboxyphenoxyacetyl, 4-trifluoromethylphenoxyacetyl, 4-trifluoromethoxyphenoxyacetyl, 4-chlorophenoxyacetyl, 4-nitrophenoxyacetyl, 4-fluorophenoxyacetyl, cyclohexyloxyacetyl, phenylsulfonylacetyl, pentafluorophenoxyacetyl, 2 and 4 formylphenoxyacetyl and 4-cyanophenoxyacetyl.

6. A compound according to claim 1 selected from the group consisting of salts of:

4'-demethyl-4'-deoxy-4'-phosphate-4-O-(2,3-bisphenoxyacetyl-4,6-ethylidene-β-D-glucosyl) epipodophyllotoxin, 4'-demethyl-4'-di(carboxymethyl)aminocarbonyl-4-O-(2,3-bisphenoxyacetyl-4,6-ethylidene-β-D-glucosyl) epipodophyllotoxin, 4'-demethyl-4'-phosphonoacetyl-4-O-(2,3-bisphenoxyacetyl-4,6-ethylidene-β-D-glucosyl) epipodophyllotoxin, 4'-demethyl-4'-deoxy-4'-phosphate-4-O-(2,3-bis(4-trifluoromethylphenoxyacetyl)-4,6-ethylidene-β-D-glucosyl)epipodophyllotoxin, 4'-demethyl-4'-di(carboxymethyl)aminocarbonyl-4-O-(2,3-bis(4-trifluoromethoxyphenoxyacetyl)-4,6-ethylidene-β-D-glucosyl)epipodophyllotoxin, 4'-demethyl-4'-deoxy-4'-phosphate-4-O-(2,3-bis(4-trifluoromethoxyphenoxyacetyl)-4,6-ethylidene-β-D-glucosyl)epipodophyllotoxin, 4'-demethyl-4'-phosphonoacetyl-4-O-(2,3-bis(4-trifluoromethoxyphenoxyacetyl)-4,6-ethylidene-β-D-glucosyl)epipodophyllotoxin, 4'-demethyl-4'-(4-phosphonooxyphenoxyacetyl)-4-O-(2,3-bis(4-phosphonooxyphenoxyacetyl)-4,6-ethylidene-β-D-glucosyl)epipodophyllotoxin, 4'-demethyl-4'-deoxy-4'-phosphate-4-O-(2,3-bis(4-phosphonooxyphenoxyacetyl)-4, -ethylidene-β-D-glucosyl)epipodophyllotoxin, 4'-demethyl-4'-di(carboxymethyl)aminocarbonyl-4-O-(, 3-biscyclohexyloxyacetyl-4,6-ethylidene-β-D-glucosyl)epipodophyllotoxin, 4'-demethyl-4'-deoxy-4'-phosphate-4-O-(2-,3-biscyclohexyloxyacetyl)-4,6-ethylidene-β-D-glucosyl) epipodophyllotoxin, 4'-demethyl-4'-(3-quinuclidinylaminocarbonyl)-4-O-(2,3-bis(3,4-methylenedioxyphenoxyacetyl)-4,6-ethylidene-β-D-glucosyl)epipodophyllotoxin, 4'-demethyl-4'-deoxy-4'-phosphate-4-O-(2,3-bis(3,4-methylenedioxyphenoxyacetyl)-4,6-ethylidene-β-D-glucosyl)epipodophyllotoxin, 4'-demethyl-4'-deoxy-4'-phosphate-4-O-(2,3bis(2,3,4,5,6-pentafluorophenoxyacetyl)-4,6-ethylidene-β-D-glucosyl)epipodophyllotoxin, 4'-demethyl-4'-deoxy-4'-phosphate-4-O-(2,3-bis(4-fluorophenoxyacetyl)-4,6-ethylidene-β-D-glucosyl) epipodophyllotoxin, 4'-demethyl-4'-deoxy-4'-(3-quinuclidinylaminocarbonyl)-4-O-(2,3-bis(4-chlorophenoxyacetyl)-4,6-ethylidene-β-D-glucosyl) epipodophyllotoxin, 4'-demethyl-4'-deoxy-4'-phosphate-4-O-(2,3-bis(4-chlorophenoxyacetyl)-4,6-ethylidene-β-D-glucosyl) epipodophyllotoxin, 4'-demethyl-4'-deoxy-4'-phosphate-4-O-(2,3-bisphenylsulfonylacetyl)-4,6-ethylidene-β-D-glucosyl) epipodophyllotoxin, 4'-demethyl-4'-(4-carboxyphenoxyacetyl)-4-O-(2,3-bis (4-carboxyphenoxyacetyl)-4,6-ethylidene-β-D-glucosyl)epipodophyllotoxin, 4'-demethyl-4'-(4-carboxymethylphenoxyacetyl)-4-O-(2,3-bis(4-carboxymethylphenoxyacetyl)-4,6-ethylidene-β-D-glucosyl)epipodophyllotoxin, 4'-demethyl-4'-(4-carboxymethoxyphenoxyacetyl)-4-O-(2,3-bis(4-carboxymethoxyphenoxyacetyl)-4,6-ethylidene-β-D-glucosyl)epipodophyllotoxin, 4'-demethyl-4-O-(2,3-bis(4-carboxymethylphenoxyacetyl)-4,6-ethylidene-β-D-glucosyl)epipodophyllotoxin, 4'-demethyl-4-O-(2,3-bis(4-carboxymethylphenoxyacetyl)-4,6-ethylidene-β-D-glucosyl)epipodophyllotoxin, 4'-demethyl-4'-(3-quinuclidinylaminocarbonyl)-4-O-(2,3-bis(4-nitrophenoxyacetyl)-4,6-ethylidene-β-D-glucosyl)epipodophyllotoxin, 4'-demethyl-4'-deoxy-4'-phosphate-4-O-(2,3-bis(4-methylenedioxyphenoxyacetyl)-4,6-ethylidene-β-D-glucosyl)epipodophyllotoxin, 4'-demethyl-4'-deoxy-4'-phosphate-4-O-(2,3-bis(4-methylenedioxyphenoxyacetyl)-4,6-ethylidene-β-D-glucosyl)epipodophyllotoxin, 4'-demethyl-4'-deoxy-4'-phosphate-4-O-(2,3-bis(4-cyanophenoxyacetyl-4,6-ethylidene-β-D-glucosyl)epipodophyllotoxin, 4'-demethyl-4'-deoxy-4'-phosphate-4-O-(2,3-bis(4-nitrophenoxyacetyl)-4,6ethylidene-β-D-glucosyl)epipodophyllotoxin, 4'-demethyl-4'-deoxy-4'-phosphate-4-O-(2,3-bis(4-methylphenoxyacetyl)-4,6-ethylidene-β-D-glucosyl)epipodophyllotoxin, 4'-demethyl-4-O-(2,3-bis(4-phosphonooxyphenoxyacetyl)-4,6-ethylidene-β-D-glucosyl)epipodophyllotoxin, and 4'-demethyl-4'-deoxy-4'-phosphate-4-O-(2,3bis(4-hydroxyphenoxyacetyl)-4,6-ethylidene-β-D-glucosyl)epipodophyllotoxin and their therapeutically acceptable and water-soluble inorganic acids or bases.

7. A compound according to claim 6, wherein the compound has an acid function or a basic function, and the acid function or basic function of the compound is salified by an agent, and the agent salifying the acidic functions are amines and the agent salifying the basic functions are inorganic or organic acids.

8. A process for the preparation of a compound according to claim 1 characterized in that a glycosylated intermediate of formula

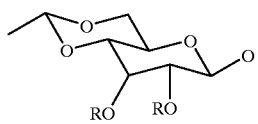

is reacted with an intermediate III

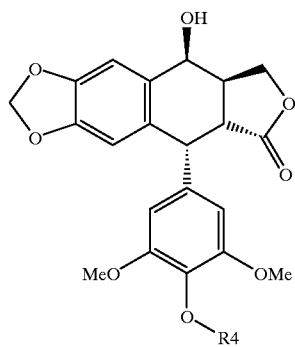

for which R is as defined in claim 1 and R4 is a protecting group, which product is deprotected in order to obtain the compounds of formula I.

9. A process for the preparation of a compound according to claim 1 wherein the etoposide protected in position 4' with a benzyloxycarbonyl or quinuclidene carbamate group of formula V

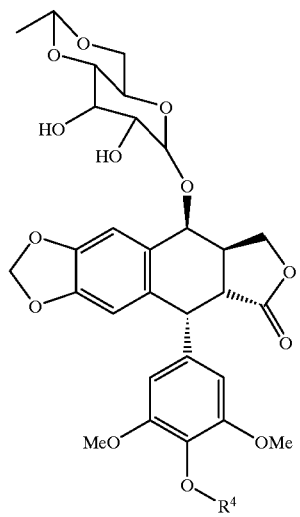

in which $R^4$ is a protecting group reacted with an acylating reagent of A—Z—$CH_2$CO type to give, after hydrogenolysis or hydrolysis, the compound of formula I.

10. A process for the preparation of the salt of a compound according to claim 1 wherein the obtained compound of claim 1, when acidic, is treated with a stoichiometric amount of base, or of ion exchange resin, and freeze-drying or crystallization is carried out.

11. A process for the preparation of the salt of a compound according to claim 1 wherein the obtained compound of claim 1, when basic, is treated with a stoichiometric amount of the acid and lyophilization or crystallization is carried out.

12. A pharmaceutical composition that comprises at least one compound of formula I of claim 1 and a suitable excipient.

13. A method of treating at least one condition selected from group consisting of alveolar lung cancer, embryonic tumors, neuroblastomas, cancer of the kidney, pediatric tumors, hodgkinian and nonhodgkinian lymphomas, acute leukemias, placental choriocarcinomas and mammary adenocarcinomas, or to increase the therapeutic efficacy of topoisomerase II-inhibitor compounds for the treatment of tumors which do not respond to the usual therapies comprising administering a therapeutically effective amount of a compound of claim 1 to a host in need of such treatment.

14. A method of treating rheumatoid arthritis, or complaints caused by human papilloma virus comprising administering a therapeutically effective amount of a compound of claim 1 to a host in need of such treatment.

* * * * *

UNITED STATES PATENT AND TRADEMARK OFFICE
CERTIFICATE OF CORRECTION

PATENT NO.    : 6,107,284
DATED         : August 22, 2000
INVENTOR(S)   : T. Imbert et al.

It is certified that error appears in the above-identified patent and that said Letters Patent is hereby corrected as shown below:

Column 1
Line 41, please delete "patient" and insert --patents--.

Column 2
Line 36, please delete "R'R" and insert --R'≠R--.

Column 3
Line 38, please delete "have" and insert --having--.

Column 4
Line 24, please delete "giving I (R'=H)" and insert --giving I (R'≠H)--.

Column 7
Line 56, please delete "H$_S$" and insert --H$_8$--.
Line 61, please delete "σ" and insert --υ--.

Column 8
Line 7, please delete "σ" and insert --υ--.
Line 40, please delete "R' =phosph" and insert --R' =phosphate--.

Column 9
Line 10, please delete "R' =phosph" and insert --R' =phosphate--.
Line 30, please delete "R' =phosph" and insert --R' =phosphate--.
Line 55, please delete "R' =phosph" and insert --R' =phosphate--.

Column 10
Line 5, please delete the structure and replace with the following structure:

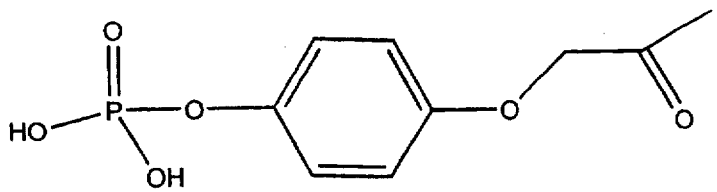

UNITED STATES PATENT AND TRADEMARK OFFICE
CERTIFICATE OF CORRECTION

PATENT NO. : 6,107,284
DATED : August 22, 2000
INVENTOR(S) : T. Imbert et al.

It is certified that error appears in the above-identified patent and that said Letters Patent is hereby corrected as shown below:

Column 10 (con't)
Line 60, please delete "R' =-PO$_3$H" and insert --R' =-PO$_3$H$_2$--.
Line 31, please delete "σ" and insert --υ--.
Line 46, please delete "σ" and insert --υ--.

Column 11
Line 9, please delete "σ" and insert --υ--.

Column 12
Line 32, please delete "σ" and insert --υ--.
Line 50, please delete "R' =COC$_2$HPO$_3$H$_2$" and insert --R' = COCH$_2$PO$_3$H$_2$--.

Column 13
Line 19, please delete "σ" and insert --υ--.
Line 39, please delete "R' =COCH$_2$PO(OH$_2$)" and insert --R' = COCH$_2$PO(OH)$_2$--.
Line 59, please delete "700" and insert --740--.
Line 66, please delete "σ" and insert --υ--.

Column 14
Line 58, please delete "σ" and insert --υ--.

Column 15
Line 6, please delete "R'=CON(C$_2$HCOOH$_2$)" and insert --R' =CON(CH$_2$CO$_2$H)$_2$--.
Line 30, please delete "R'=CON(C$_2$HCOOH$_2$)" and insert --R' =CON(CH$_2$CO$_2$H)$_2$--.
Line 40, plese delete "N$_{47}$" and insert --H$_{47}$--.
Line 55, please delete "R'=CON(C$_2$HCOOH$_2$)" and insert --R' =CON(CH$_2$CO$_2$H)$_2$--.

Column 17
Line 12, please delete "σ" and insert --υ--.

Column 19
Line 5, please delete "phospha" and insert --phosphate--.
Line 40, please delete "phospha" and insert --phosphate--.

UNITED STATES PATENT AND TRADEMARK OFFICE
CERTIFICATE OF CORRECTION

PATENT NO.    : 6,107,284
DATED         : August 22, 2000
INVENTOR(S)   : T. Imbert et al.

It is certified that error appears in the above-identified patent and that said Letters Patent is hereby corrected as shown below:

Column 20
Line 5, please delete "phosph" and insert --phosphate--.
Line 35, please delete the structure, and insert the following structure:

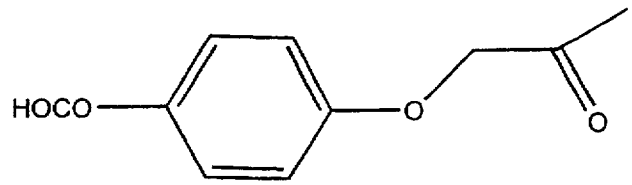

Column 21
Line 35, please delete the structure, and insert the following structure:

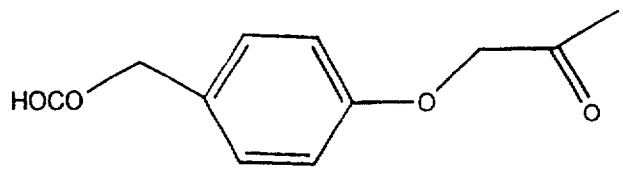

Line 55, please delete the structure, and insert the following structure:

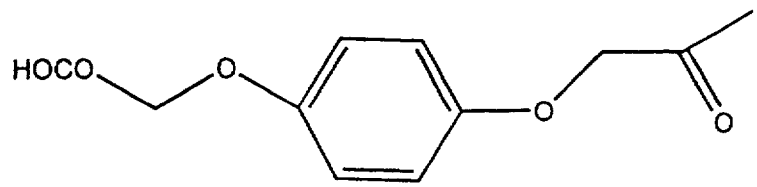

UNITED STATES PATENT AND TRADEMARK OFFICE
CERTIFICATE OF CORRECTION

PATENT NO.   : 6,107,284
DATED        : August 22, 2000
INVENTOR(S)  : T. Imbert et al It is certified that error appears in the above-identified patent and that said Letters Patent is hereby corrected as shown below:

Column 22
Line 15, please delete "$P_3OH_2$" and insert -- $PO_3H_2$ --.
Line 23, please insert -- Preparation of the intermediates (route B) 4'-demethyl-4'-(3-quinuclidinylaminocarbonyl)-4-O-(2,3-bis(4-chlorophenoxyacetyl)-4,6-ethylidene-β-D-glucosyl)epipodophyllotoxin. --.
Line 57, please delete "1.97" and insert -- 1.97g --.

Column 24
Line 29, please delete $HOCOC_2OCH_2CO$" and insert -- $HOCOCH_2OCH_2CO$ --.
Line 57, please delete "that" and insert -- an --.

Column 25
Line 45, please delete "10.98.88" and insert -- 1098.88 --.

Claim 1
Line 58, please delete "$CH_2OP_3H_2$" and insert -- $CH_2PO_3H_2$ --.

Signed and Sealed this

Twenty-eighth Day of August, 2001

*Attest:*

*Attesting Officer*

NICHOLAS P. GODICI
*Acting Director of the United States Patent and Trademark Office*